United States Patent

Toda

Patent Number: 5,276,214
Date of Patent: Jan. 4, 1994

[54] OPTICALLY ACTIVE BIPHENYL DERIVATIVE AND PROCESS FOR OPTICAL RESOLUTION

[75] Inventor: Fumio Toda, Ehime, Japan

[73] Assignee: Daicel Chemical Industries, Ltd., Osaka, Japan

[21] Appl. No.: 993,116

[22] Filed: Dec. 18, 1992

Related U.S. Application Data

[62] Division of Ser. No. 646,096, Jan. 25, 1991, Pat. No. 5,202,504.

[30] Foreign Application Priority Data

Oct. 29, 1990 [JP] Japan ................... 2-293412

[51] Int. Cl.$^5$ .................................. C07B 57/00
[52] U.S. Cl. ...................... 568/730; 568/634; 568/707; 568/715; 568/716; 568/722; 568/774; 568/775
[58] Field of Search ............. 568/631, 634, 637, 650, 568/707, 568/715, 730, 763, 794, 809, 811, 812, 722, 807, 716, 707, 774, 775

[56] References Cited

U.S. PATENT DOCUMENTS

| | | | |
|---|---|---|---|
| 2,651,644 | 9/1953 | Gisvold et al. | 568/730 |
| 5,053,548 | 10/1991 | Tanaka et al. | 568/730 |
| 5,130,356 | 7/1992 | Feuerherd et al. | 568/730 |
| 5,202,504 | 4/1993 | Toda | 568/730 |

FOREIGN PATENT DOCUMENTS

| | | | |
|---|---|---|---|
| 01810044 | 9/1985 | Japan | 568/730 |

*Primary Examiner*—Werren B. Lone
*Attorney, Agent, or Firm*—Flynn, Thiel, Boutell & Tanis

[57] ABSTRACT

A biphenyl compound having the formula (I) is newly separated into its optical active compound, and useful as an optically separating agent:

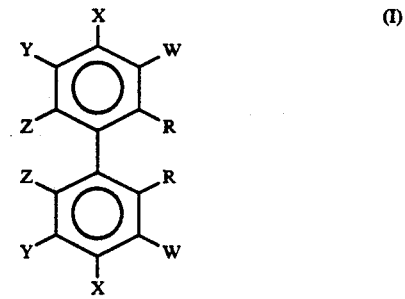

wherein W, X and Y are each an atom or atomic group selected from among H, F, Cl, Br, I, $CH_3$, $CF_3$, OH, $OCH_3$, $NH_2$ and $N(CH_3)_2$ and Z is an atom or atomic group selected from among Cl, Br, I, $CH_3$ and $OCH_3$, R is an atomic group having 1 to 20 carbon atoms and containing a polar functional group selected from among

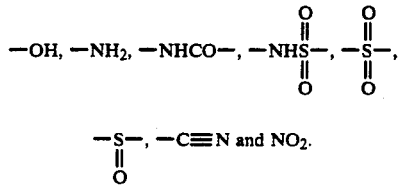

7 Claims, No Drawings

OPTICALLY ACTIVE BIPHENYL DERIVATIVE AND PROCESS FOR OPTICAL RESOLUTION

This is a division of Ser. No. 07/646,096, filed Jan. 25, 1991 now U.S. Pat. No. 5,202,504.

FIELD OF INDUSTRIAL APPLICATION

The present invention relates to a novel optically active biphenyl derivative, a process for optical resolution using the same, and a process of examining a compound for optical isomer ratios or for absolute configurations of optically active substances by the use of the same.

An optically active compound is generally useful as a drug, pesticide, insecticide, herbicide, perfume, ferroelectric liquid crystal, a raw material from which the foregoing is obtained or as a reagent for optical resolution of another racemate into its optical active compound.

PRIOR ARTS

There have already been known many compounds which have the ability of forming a crystal, preferentially together with either of the optical isomers of another compound; to thereby resolve the optical isomers (such a compound is hereinafter referred to as the "resolving agent"). However, in many cases, the resolving agent and the compound to be resolved therewith must be a combination of a base and an acid (or vice versa).

Recently, it has been ascertained by the inventors of the present invention that optically active 2,2'-dihydroxy-1,1'-binaphthyl, 10,10'-dihydroxy-9,9'-biphenanthryl and 1,6-bis(o-chlorophenyl)-1,6-diphenylhexa-2,4-diyne-1,6-diol have the above-mentioned ability. However, these resolving agents cannot resolve all compounds, and can be applied only to a group of compounds which are limited in some measure. Therefor, the development of a novel resolving agent for optical resolution which can be applied to as many compounds as possible has been needed.

Meanwhile, the determination of the purity of an optically active substance as well as the preparation of an optically active substance is difficult. A conventional process for this determination involves using a chiral shift reagent. This process is characterized by adding a compound which is optically active and has an influence on the chemical shift of an atom (particularly a proton) present in the neighborhood (such a compound is called "chiral shift reagent") in the NMR spectroscopic analysis of an optically active substance to thereby make the NMR signals of the optical isomers which ought to appear at the same chemical shift (at the same spectral position) in themselves appear at chemical shifts different from each other and determining the optical isomer ratio based on the intensities of the signals thus separated. The chiral shift reagent to be used in the above process generally contains a lanthanide metal such as europium which not only is an expensive rare metal, but also tends to decompose in the presence of water or the like, thus being difficult handle. Further, the NMR signals are widened by the influence of the metal to make the discrimination between the signals difficult, so that the compounds to which such a chiral shift reagent is applicable are limited. Therefor, the development of a novel chiral shift reagent free from such a metal has been needed.

For the above-mentioned reasons, the present invention aims at developing a novel resolving agent or a novel chiral shift reagent. Needless to say, not all compounds function as a resolving agent or as a chiral shift reagent, as only limited optically active substances can function as much. Further, there have been no clear guidelines on the structural features of an optically active substance useful as a reagent as described above.

SUMMARY OF THE INVENTION

The inventors of the present invention have intensively studied to solve the above problems and have found that an optically active biphenyl derivative having a proper functional group exhibits excellent performances as a resolving agent or as a chiral shift reagent. The present invention has been accomplished on the basis of this finding.

Namely, the present invention provides a novel optically active biphenyl derivative represented by the general formula (I):

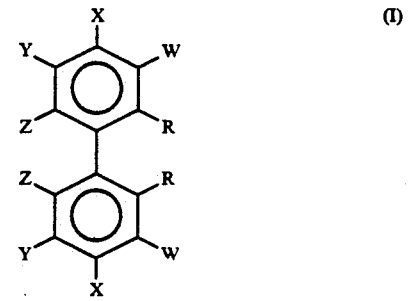

wherein W, X and Y are each an atom or atomic group selected from among H, F, Cl, Br, I, $CH_3$, $CF_3$, OH, $OCH_3$, $NH_2$ and $N(CH_3)_2$ and Z is an atom or atomic group selected from among Cl, Br, I, $CH_3$ and $OCH_3$, with the proviso that the atoms represented by H in these alternatives may be either H or D (deuterium); R is an atomic group having 1 to 20 carbon atoms and containing a polar functional group selected from among

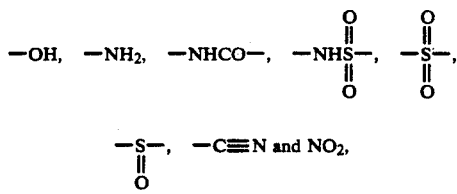

wherein preferably all of the carbon atoms except for one or two of them are included in one or two cyclic atomic groups, preferably phenyl or cyclohexyl group(s), and particularly preferably R is a diarylhydroxymethyl group represented by the formula: —C-(OH)Ar$_2$ (wherein Ar is an aromatic group represented by a phenyl group and which may have any substituent);

a process for optical resolution using a separating agent containing said optically active biphenyl derivative; and a process of examining a compound for optical isomer ratios or for absolute configurations of optically active substances by the use of said optically active biphenyl derivative as a chiral shift reagent.

The optical activity of the biphenyl derivative according to the present invention can be confirmed by the fact that it exhibits optical rotation. Alternatively, the derivative can be ascertained to be optically active when the optical isomer ratio is not precisely 1:1; as determined by, e.g., liquid chromatography with a separatory column for optical isomers. Needless to say, it is preferable that the optical purity of the derivative to be used as a resolving agent or a chiral shift reagent be as high as possible.

Although the biphenyl derivative of the present invention may be prepared by any process, it can be relatively easily prepared by chemically replacing the substituents of a known optically active biphenyl derivative. For example, 4,4',6,6'-tetrachloro-2,2'-bis(hydroxydiphenylmethyl)biphenyl can be prepared by reacting 4,4',6,6'-tetrachlorobiphenyl-2,2'-dicarboxylic acid with a phenyl Grignard reagent to replace the carboxyl groups with diphenylhydroxymethyl groups.

Optical resolution using the biphenyl derivative of the present invention as a resolving agent may be conducted in any manner. Preferably, it is conducted through the formation of a clathrate compound of the resolving agent with a compound to resolved. As will be described in relation to the utilization of the derivative as a chiral shift reagent, however, the derivative exhibits different interactions on the optical isomers of the compound to be resolved respectively, not only in a crystal structure but also in a solution. Accordingly, it is apparent that the resolving power of the derivative is exhibited not only in the above process through the formation of the clathrate compound. For example, optical resolution according to the present invention may be conducted by liquid or gas chromatography using the derivative chemically or physically immobilized on a support as a packing. Further, in the process through the formation of a crystal of the derivative with the compound to be resolved, the formation of the crystal and the isolation of the objective compound from the crystal may be each conducted by any method.

When the biphenyl derivative of the present invention is used as a chiral shift reagent, the compound to be examined for optical purity is dissolved in a proper solvent (generally so as to give several steps of concentrations), followed by the addition of a proper amount of a chiral shift reagent. When the obtained solution is subjected to NMR spectroscopic analysis, in many cases, one peak (or one set of peaks) which is exhibited in a case wherein no chiral shift reagent is contained, is split into two peaks (or two sets of peaks), which are assignable to optical isomers respectively. The optical purity can be calculated from the area intensities of the peaks. Further, the positions of the peaks can be experimentally correlated with the structures (absolute configurations) of the optical isomers.

EXAMPLE

The present invention will now be described in more detail by referring to the following Examples, though it is needless to say that the present invention is not limited to them.

EXAMPLE 1

4,4',6,6'-Tetrachlorobiphenyl-2,2'-dicarboxylic acid was optically resolved according to the diastereomer method described in E. R. Atkinson, Org. Prep. Proced. Int., 3, 71 (1971). The obtained optically active substance was treated with phenylmagnesium bromide to give optically active 4,4',6,6'-tetrachloro-2,2'-bis(hydroxydiphenylmethyl)biphenyl.

The physical properties of the raw material and the product are given below.

| Raw material | Product | |
|---|---|---|
| angle of rotation | angle of rotation $[\alpha]_D$ (c = 0.1, chloroform) | m.p. (°C.) |
| + | +110° | 231 to 233 |
| − | −110° | 231 to 233 |

EXAMPLE 2

1.5 g of (+)-4,4',6,6'-tetrachloro-2,2'-bis(hydroxydiphenylmethyl)biphenyl and 0.45 g of 3-methyl-2-pyrrolidone (racemic mixture) were dissolved in 6 ml of a benzene-hexane mixture having a volume ratio of 1. The obtained solution was allowed to stand at a room temperature for 24 hours to give a complex of (+)-4,4',6,6'-tetrachloro-2,2'-bis(hydroxydiphenylmethyl)biphenyl with 3-methyl-2-pyrrolidone (1:1) as a colorless crystal. This crystal was recrystallized five times to give 1.12 g of a pure crystal [m.p.: 213° to 214° C., $[\alpha]_D+87.7°$ (c=0.1, chloroform)]. This pure crystal was heated in a vaccum to give 0.14 g of (−)-3-methyl-2-pyrrolidone [$[\alpha]_D-60.6°$ (c=0.3, benzene), optical purity: 100% e.e., yield: 62%]. On the other hand, the mother liquor of the recrystallization gave 0.25 g of (+)-3-methyl-2-pyrrolidone (47% e.e.).

EXAMPLE 3

The (+)-3-methyl-2-pyrrolidone (47% e.e.) prepared in Example 2 and (−)-4,4',6,6'-tetrachloro-2,2'-bis(hydroxydiphenylmethyl)biphenyl were treated in a similar manner to that of Example 2 to give a complex (1:1) as a crystal. This crystal was further treated in a similar manner to that of Example 2 to give 0.1 g of (+)-3-methyl-2-pyrrolidone [$[\alpha]_D+60.6°$ (c=0.3, benzene), 100% e.e.].

EXAMPLE 4

The NMR chemical shifts of various racemic mixtures (samples) listed in Table 1 were measured in deuteriochloroform by using (+)-4,4',6,6'-tetrachloro-2,2'-bis(hydroxydiphenylmethyl)biphenyl (hereinafter abbreviated to "Optically active substance 1") as a chiral shift reagent. The measurement was conducted by using a solution containing 0.02 g of a sample per ml of deuteriochloroform with respect to a case wherein no optically active substance 1 was contained and cases wherein it was contained in an amount of 1 or 2 mol per mol of the sample, thus determining the chemical shift of the proton represented in italic type in the structural formula of the sample. The results are given in Table 1.

TABLE 1

Relationship between chemical shift and molar amount of Optically active substance 1

| Sample | Chemical shift (ppm) molar ratio of Optically active substance 1 to sample | | |
|---|---|---|---|
| | 0 | 1 | 2 |
| PhCH—CH₃<br>\|<br>NH₂ | 1.377 | 1.234<br>1.251 | 1.065<br>1.096 |

TABLE 1-continued
Relationship between chemical shift and molar amount of Optically active substance 1

| Sample | Chemical shift (ppm) molar ratio of Optically active substance 1 to sample | | |
|---|---|---|---|
| | 0 | 1 | 2 |
| Me-N(ring)-CH₃ with N-Me | 1.038 | 0.979 1.000 | 0.938 0.983 |
| pyrrolidinone with CH₃ | 1.196 | 1.081 1.100 | 0.958 1.017 |
| CH₃-pyrrolidinone | 1.220 | 1.033 1.058 | 0.956 0.998 |
| PhCHCH₃ \| OH | 4.860 | 4.779 | 4.635 4.676 |
| CH₃—CHC≡N \| OH | 4.605 | 4.295 4.441 | |
| CH₃ \| i-Pr—C—C≡N \| OH | 1.552 | 1.467 1.483 | 1.407 1.440 |
| n-Oct—SO—CH₃ | 2.550 | 2.227 2.280 | |
| pyridyl-SO—CH₃ | 2.853 | 2.623 2.667 | |
| Ph—SO—CH₃ ‖ NH | 2.703 | 2.444 2.500 | |
| p-Tol—SeO—CH₃ | 2.587 | 2.167 2.283 | |
| p-Tol—NO—CH₃ \| CH₂CH₃ | 3.483 | 2.910 2.943 | 2.743 2.813 |
| p-Tol—PO—OCH₃ \| CH₃ | 1.643 3.588 | 1.414 1.432 3.430 3.450 | 1.313 1.336 3.335 3.365 |
| Ph—PO—C≡CH \| CH₃ | 1.928 | 1.610 1.661 | |
| Ph—AsO—CH₃ | 1.807 | 1.433 1.457 | 1.204 1.329 | note)
Ph represents a phenyl group, Me represents a methyl group, i-Pr represents an isopropyl group, n-Oct represents a n-octyl group and p-Tol represents a p-tolyl group.

As is apparent from the results given in Table 1, one chemical shift exhibited in a case wherein no optically active substance 1 was added was split into two chemical shifts by the addition of optically active substance 1.

I claim:

1. A process for the optical resolution of a racemic mixture, comprising a step of contacting said racemic mixture with a separating agent containing an optically active biphenyl derivative, said optically active biphenyl derivative being represented by the general formula (I):

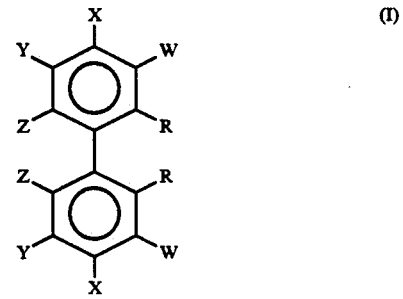

wherein W, X and Y are selected from among H, F, Cl, Br, I, CH₃, CF₃, OH, OCH₃, NH₂ and N(CH₃)₂ and Z is selected from among Cl, Br, I, CH₃ and OCH₃; R is a group having 1 to 20 carbon atoms and containing a polar functional group selected from among

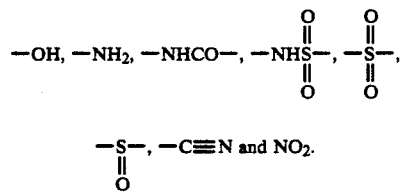

2. A process for optical resolution as set forth in claim 1, wherein said optical resolution is conducted through the formation of a crystal comprising said optically active biphenyl derivative and the compound to be optically resolved.

3. A process of examining a compound for optical isomer ratio or for absolute configurations of optically active substances, said process comprising the step of subjecting the compound to NMR spectroscopic analysis in the presence of an optically active biphenyl derivative represented by the general formula (I):

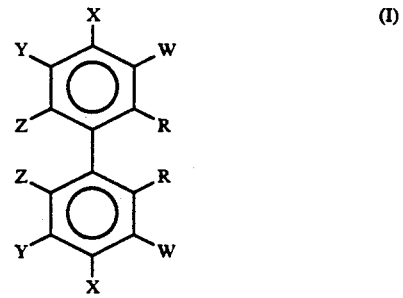

wherein W, X and Y are selected from among H, F, Cl, Br, I, CH₃, CF₃, OH, OCH₃, NH₂ and N(CH₃)₂ and Z is selected from among Cl, Br, I, CH₃ and OCH₃; R is a group having 1 to 20 carbon atoms and containing a polar functional group selected from among

—OH, —NH₂, —NHCO—, —NHS(=O)(=O)—, —S(=O)(=O)—,

—S(=O)—, —C≡N and NO₂, and determining the ratio of the absolute configurations based on the obtained spectrum.

4. A process for the optical resolution of a racemic mixture selected from the group consisting of

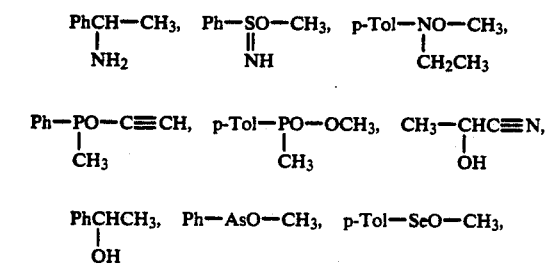

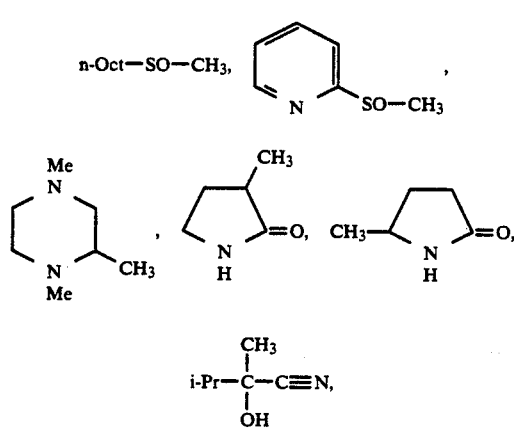

comprising a step of contacting said racemic mixture with a separating agent containing an optically active biphenyl derivative, said optically active biphenyl derivative being represented by the general formula (I):

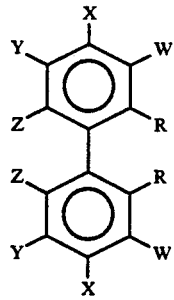
(I)

wherein W, X and Y are selected from among H, F, Cl, Br, I, CH₃, CF₃, OH, OCH₃, NH₂ and N(CH₃)₂ and Z is selected from among Cl, Br, I, CH₃ and OCH₃; R is a group having 1 to 20 carbon atoms and containing a polar functional group selected from among

—OH, —NH₂, —NHCO—, —NHS(=O)(=O)—, —S(=O)(=O)—,

—S(=O)—, —C≡N and NO₂.

5. A process for examining a compound for optical isomer ratio or for absolute configurations of optically active substances, said compound selected from the group consisting of

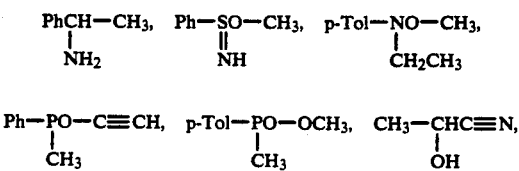

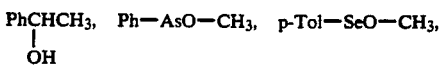

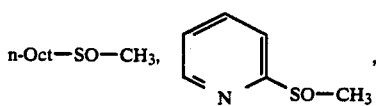

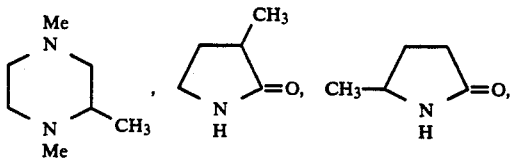

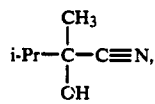

said process comprising the step of subjecting the compound to NMR spectroscopic analysis in the presence of an optically active biphenyl derivative represented by the general formula (I):

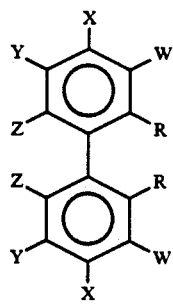
(I)

wherein W, X and Y are selected from among H, F, Cl, Br, I, CH₃, CF₃, OH, OCH₃, NH₂ and N(CH₃)₂ and Z is selected from among Cl, Br, I, CH₃ and OCH₃; R is a group having 1 to 20 carbon atoms and containing a polar functional group selected from among

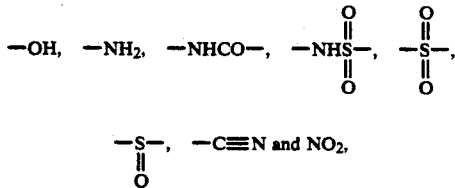

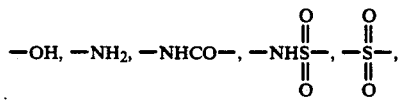

and determining the ratio of the absolute configuration based on the obtained spectrum.

6. A process for the optical resolution of a racemic mixture into an optically active member having a utility as a drug, pesticide, insecticide, herbicide, perfume or ferroelectric liquid crystal, comprising a step of contacting said racemic mixture with a separating agent containing an optically active biphenyl derivative, said optically active biphenyl derivative being represented by the general formula (I):

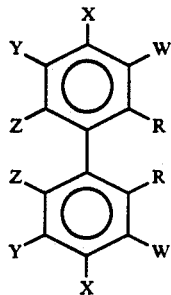
(I)

wherein W, X and Y are selected from among H, F, Cl, Br, I, $CH_3$, $CF_3$, OH, $OCH_3$, $NH_2$ and $N(CH_3)_2$ and Z is selected from among Cl, Br, I, $CH_3$ and $OCH_3$; R is a group having 1 to 20 carbon atoms and containing a polar functional group selected from among

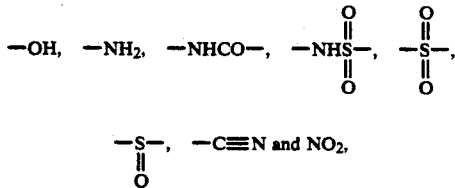

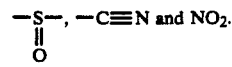

7. A process for examining a compound for optical isomer ratio or for absolute configurations of optically active substances, said compound, when optically resolved, yielding an optically active member having a utility as a drug, pesticide, insecticide, herbicide, perfume or ferroelectric liquid crystal, said process comprising the step of subjecting the compound to NMR spectroscopic analysis in the presence of an optically active biphenyl derivative represented by the general formula (I):

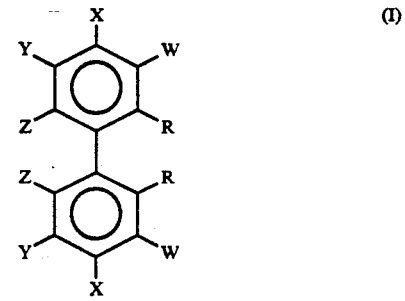
(I)

wherein W, X and Y are selected from among H, F, Cl, Br, I, $CH_3$, $CF_3$, OH, $OCH_3$, $NH_2$ and $N(CH_3)_2$ and Z is selected from among Cl, Br, I, $CH_3$ and $OCH_3$; R is a group having 1 to 20 carbon atoms and containing a polar functional group selected from among

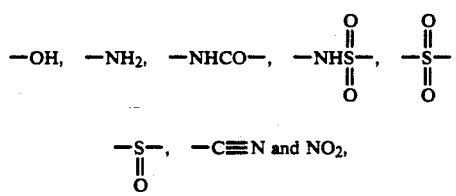

and determining the ratio of the absolute configurations based on the obtained spectrum.

* * * * *

UNITED STATES PATENT AND TRADEMARK OFFICE
CERTIFICATE OF CORRECTION

PATENT NO. : 5 276 214

DATED : January 4, 1994

INVENTOR(S) : Fumio Toda

It is certified that error appears in the above-identified patent and that said Letters Patent is hereby corrected as shown below:

Column 10, line 45; delete "X".

Signed and Sealed this

Thirty-first Day of May, 1994

*Attest:*

BRUCE LEHMAN

*Attesting Officer*     *Commissioner of Patents and Trademarks*